United States Patent [19]
Bronson et al.

[11] Patent Number: 5,667,978
[45] Date of Patent: Sep. 16, 1997

[54] ANTIBODY TO THE NEURAL CELL ADHESION MOLECULE AND METHODS OF USE

[75] Inventors: Duane David Bronson, Chapel Hill; John Jacob Hemperly, Apex, both of N.C.

[73] Assignee: Becton, Dickinson and Company, Franklin Lakes, N.J.

[21] Appl. No.: 642,288

[22] Filed: May 3, 1996

Related U.S. Application Data

[60] Division of Ser. No. 405,598, Mar. 16, 1995, Pat. No. 5,591,432, which is a continuation-in-part of Ser. No. 18,664, Feb. 17, 1993, abandoned.

[51] Int. Cl.$^6$ .............. A61K 39/395; C07K 16/28; A61B 17/04; G01N 33/53
[52] U.S. Cl. .............. 435/7.1; 435/7.2; 435/7.92; 435/960; 424/141.1; 424/152.1; 424/156.1; 424/178.1; 424/143.1; 530/387.1; 530/839; 606/228; 606/152
[58] Field of Search .............. 435/7.1, 7.2, 7.92, 435/7.7, 7.71, 7.72, 960; 538/387.1, 839; 424/178.1, 423, 426, 486, 141, 143.1, 152.1, 156.1; 606/228, 231, 152; 264/202

[56] References Cited

U.S. PATENT DOCUMENTS 4,955,892  9/1990  Daniloff .............. 606/152

OTHER PUBLICATIONS

Small, SJ et al 1990 J. Cel. Biol. 111:2089–2096.
Doherty P. et al 1992 Nature 356: 791–793.
Kline DG 1990 Muscle & Nerve 13:843–852.
L. L. Lanier, et al. "Molecular and Functional Analysis of Human Natural Killer Cell–Associated neural Cell Adhesion Molecule (N–CAM/CD56)" *J. Immunol.* 146:4421–4426 (1991).
B. R. Seckel "Enhancement of Peripheral Nerve Regeneration" *Muscle & Nerve* 13:785–800 (1990).
L. G. Remsen, et al. "Antibodies to the Neural Cell Adhesion Molecule Disrupt Functional Recovery in Injured Nerves" *Exp. Neurol.* 110:268–273 (1990).
K. J. Tomaselli and L. F. Reichardt "Integrins, Cadherins, and Cell Adhesion Molecules of the Immunoglobulin Superfamily: Neuronal Receptors That Regulate Axon Growth and Guidance" *The Assembly of the Nervous System*, Alan R. Liss, Inc., 1989, pp. 81–108.

*Primary Examiner*—Lila Feisee
*Assistant Examiner*—John Lucas
*Attorney, Agent, or Firm*—Donna R. Fugit

[57] ABSTRACT

The present invention provides an anti-N-CAM monoclonal antibody which enhances, rather than inhibits, neurite outgrowth both in vitro and in vivo. The antibody has positive regulatory effects on nerve cells of both the central and peripheral nervous systems, and is useful for enhancing neurite outgrowth in in vitro studies and for improving nerve regeneration and repair in vivo.

3 Claims, 4 Drawing Sheets

ANTIBODY TO THE NEURAL CELL ADHESION MOLECULE AND METHODS OF USE

This is a division of application Ser. No. 08/405,598, filed Mar. 16, 1995 now U.S. Pat. No. 5,591,432, which is continuation-in-part of U.S. Ser. No. 08/018,664, filed Feb. 17, 1993 now abandoned.

FIELD OF THE INVENTION

The present invention relates to regulation of nerve growth. In particular, the invention relates to cell adhesion molecules which regulate nerve growth and antibodies to such cell adhesion molecules.

BACKGROUND OF THE INVENTION

The precise and reproducible development of the nervous system in vertebrates and invertebrates is accomplished by the directed growth of axons and dendrites (neurites) from neuronal cell bodies to their synaptic target cells. The extent and orientation of nerve growth is regulated and guided by a variety of molecules which are synthesized by neurons as well as non-neuronal cells. These regulators may be secreted or they may be immobilized on the surface of the cell which produces them. Binding of the regulator to a receptor on the neuronal cell surface causes a signal which regulates the intracellular molecules which control growth. Many types of molecules which regulate neuronal outgrowth are known. Some stimulate neurite growth (e.g., neurotrophic molecules, neurotransmitters, extracellular matrix molecules and cell adhesion molecules) while others function as inhibitors or negative regulators. The cell adhesion molecules (CAMs) are a large group of cell surface molecules which play an important role in regulating neuronal adhesion and neurite process extension. CAMs may be either $Ca^{2+}$-independent (e.g., N-CAM, contactin and L1/NgCAM) or $Ca^{2+}$-dependent (e.g., the cadherin protein family). Several of the $Ca^{2+}$-independent CAMs have been sequenced, and are structurally homologous to immunoglobulins. They are believed to mediate cell-cell adhesion by both homotypic and heterotypic binding mechanisms, and several are localized on the surfaces of axons during development. As several of the Ig homologues have been demonstrated to directly stimulate neurite outgrowth, this group of molecules is believed to play an important role in this process.

Of particular interest is the neural cell adhesion molecule, N-CAM, which serves as a ligand for homophilic adhesion between cells. N-CAM is generally recognized as a positive regulator of neuronal process outgrowth and is present in the membranes of developing neural cells and differentiated axons. Adult nerves, which normally express the adult A form of N-CAM, revert to expression of large amounts of the embryonic E form of this molecule upon injury. Antibodies to N-CAM have been shown to reduce the outgrowth of central and peripheral axons in vitro (B. R. Seckel, 1990, *Muscle & Nerve* 13:785-800), and to disrupt reinnervation and functional recovery in transected sciatic nerves in vivo, presumably due to blockage of N-CAM binding (L. G. Remsen, et al. 1990, *Exp. Neurol.* 110:268-273).

When a nerve is severed, the regions of the neurites which are distal to the break become separated from the nerve cell body and degenerate. Death and degeneration of the neurites leaves only the empty nerve sheath and this, too, eventually degenerates. In addition there is some degeneration of the proximal stump. If degeneration does not result in the death of the nerve cell body it is possible for the nerves to regenerate by re-extension of the severed axons, especially if the regeneration occurs at a sufficient distance from the nerve cell body. The newly regenerating neurites are referred to as "nerve sprouts" and grow distally toward the sheath of the distal portion of the severed nerve. If the neurites successfully enter the sheath they will often grow down its length and function may be restored. Regrowth of the neurites is impeded or prevented by scar formation, which may be stimulated by trauma caused by suturing nerve ends in an effort to maintain alignment or by other manipulations involved in nerve repair. Nerve guide repair, which uses a conduit to bridge the gap between the proximal and distal ends of the severed nerve, has provided an alternative to nerve grafting and conventional repair techniques. Nerve guide repair is also referred to as "entubulation repair". Originally, entubulation repair employed an empty plastic tube applied to the damaged nerve ends to guide regrowth. With this technique there is less trauma, as only one epineural suture in each nerve stump is usually required to hold the nerve guide in place. Nerve guide repair may also prevent or reduce ingrowth of scar tissue which may interfere with the distal migration of the nerve sprout. The proximal stump, suspended in the nerve guide, may therefore begin its distal migration without obstruction by an imperfectly aligned degenerating distal stump, scar tissue, etc.

As certain cell adhesion molecules (CAMs, e.g., N-CAM, L1 Antigen, N-cadherin, GP135), neurotrophic factors (i.e., factors which promote survival and growth of neurons such as NGF and CNTF), and neurite-promoting factors (i.e., substrate bound glycoproteins which are usally components of the basal lamina such as laminin, collagen, entactin proteoglycan, fibrinogen and fibronectin) have been found to be involved in peripheral nerve regeneration, they have been used to modify nerve guides to improve nerve repair. Madison, et al., (1988 Brain Research 447:325-334) describe a nerve guide having a lumen filled with a collagen- or laminin-containing gel. U.S. Pat. No. 5,019,087 discloses a nerve guide having walls comprising Type I collagen or laminin. U.S. Pat. No. 5,011,486 discloses nerve guides comprising porous tubular membranes having a growth-enhancing active factor incorporated within the membrane. U.S. Pat. No. 4,759,764 discloses the use of basal lamina with the cellular material removed as a nerve guide. U.S. Pat. No. 4,955,892 discloses addition of a neural cell adhesion molecule (N-CAM) to a matrix in the lumen of the guide. While N-CAM enhances nerve growth, antibodies to N-CAM reportedly disrupted recovery of muscle function when nerve guides containing such antibodies were applied to transected sciatic nerves (L. G. Remsen, et al., supra). U.S. Pat. No. 5,026,381 discloses a nerve guide with multilayered, semipermeable walls comprising Type I collagen.

In the tubular nerve guides described in the prior art, the regenerating axons grow along the inside wall of the tube, along other axons, or along Schwann cells which have previously bridged the gap between the stumps. It is therefore likely that the axon will lose positional information and waste energy by growing in nonproductive directions, as a large surface area is available for regrowth. This problem can be overcome by providing a nerve guide in the form of a fiber (i.e., a fiber nerve guide) which presents less surface area to the regenerating axon. The neurite therefore has less opportunity to lengthen its path to the target distal stump or sheath, resulting in more efficient regeneration. The fiber may be a surgical suture which is used to join a nerve bundle or fasicle of one stump of a severed nerve to the corresponding bundle of the other stump. Alternatively, the fiber nerve guide may be used in vitro to guide nerve cell outgrowth, in which case nerve cells may be placed on the fiber either as a mass of cells (e.g., a ganglion) or as dissociated cells useful for studies of individual nerve cells. A molecule which regulates neuronal process (nerve sprout) outgrowth may be applied to the surface of the fiber, i.e., layered thereon or covalently coupled to the fiber, to promote and direct this process.

SUMMARY OF THE INVENTION

The present invention provides an anti-N-CAM monoclonal antibody which enhances, rather than inhibits, neurite or neuronal process outgrowth both in vitro and in vivo. The antibody has positive regulatory effects on nerve cells of both the central and peripheral nervous systems, and is useful for enhancing neurite outgrowth in in vitro studies and for improving nerve regeneration in vivo.

DETAILED DESCRIPTION OF THE INVENTION

Figure 1:
FIG. 1 is a graph of the data generated in Example 2 comparing the performance of fiber nerve guides having different neuronal regulatory molecules on the surface.

Leu19, an anti-NCAM monoclonal antibody (Becton Dickinson Advanced Cellular Biology, San Jose, Calif.) was used to prepare an immunoaffinity column. NCAM from human adult brain was purified by standard techniques using the Leu19 affinity column. Using conventional techniques for preparation of monoclonal antibodies, mice were immunized with the immunoaffinity purified NCAM and the spleen cells were fused with murine myeloma cells. The hybridomas produced were screened for reactivity with the immunogen in ELISA assays and rescreened with synthetic peptides representing various immunoglobulin domains of NCAM. The hybridoma which produces NCAM16.2 was selected for further characterization based on its strong reactivity with the immunogen, and was deposited with the American Type Culture Collection (Rockville, Md.) under the Budapest Treaty on Feb. 2, 1993 under Accession No. HB11261. This antibody is also commercially available from Becton Dickinson Advanced Cellular Biology (San Jose, Calif.).

Several of the monoclonal antibodies isolated were characterized for their effects on neurite outgrowth. Rat cerebellar neurons (CNS) and rat dorsal root ganglia (PNS) were tested for their growth response to monoclonal antibodies NCAM16.2, NCAM14.2 and NCAM18.1, either with or without bound NCAM antigen. The antibodies were bound to plastic plates derivitized with hydrazide groups for coupling to oxidized sugars on glycoproteins (AVIDPLATE-HZ, BioProbe, Inc.). Antigen, if bound to the antibody, was applied for 1 hr. at 10 µg/ml after blocking the plate with BSA-TEST (1% bovine serum albumin in TRIS-buffered saline containing 0.5% TWEEN-20). After rinsing with PBS, the antigen was crosslinked to the antibody with glutaraldehyde for 0.5 hr., followed by an additional block with BSA-TBST. The plate was sterilized with three washes with HBSS and Pen-Strep. Neurite outgrowth in the wells containing antibody only was substantially equivalent to that in the buffer-only control well for all monoclonal antibodies except NCAM16.2. In the presence of NCAM16.2, extensive neurite outgrowth was seen in cerebellar cells after only 24 hrs., with large numbers of neurite processes reaching for considerable distances. The outgrowth-promoting effect of NCAM16.2 on dorsal root ganglion cells was smaller, but still clearly distinguishable over the other antibodies and from the buffer-only negative control. Similar effects were seen in crosslinked controls where no antigen was present and under conditions where the antigen was not crosslinked (e.g., antigen was removed by washing). Neurite outgrowth was totally inhibited when NCAM16.2 was crosslinked to its antigen by glutaraldehyde or DMP (dimethyl pimelimidate-Pierce). Over two additional days of growth, the cells treated with NCAM16.2 continued to produce extensive neurite processes, whereas those treated with the other anti-NCAM antibodies showed little, if any, neurite outgrowth.

Characterization of the epitopes recognized by the anti-NCAM monoclonal antibodies demonstrates that NCAM18.1 is directed against an intracellullar epitope and is therefore effectively a negative control antibody when used on intact cells. The epitope recognized by NCAM16.2 appears to be in the third immunoglobulin domain (Ig-3). This was determined by expressing the cloned Ig domains of N-CAM as LacZ fusion proteins in bacteria. After induction by IPTG, the reactivity of the antibodies with the fusion proteins was determined on Western blots. NCAM16.2 recognized the Ig-3 and Ig-3+4 fusion proteins, but did not recognize the fusion protein containing the Ig-4 domain alone. Ig-4 contains the VASE exon of N-CAM, and it is therefore unlikely that NCAM16.2 is directed to the VASE exon specifically.

Monoclonal antibody NCAM16.2 unexpectedly promotes neurite outgrowth from central nervous system and peripheral nervous system cells, whereas prior art anti-NCAM antibodies functioned as antagonists or inhibitors of nerve cell growth. This effect is seen both in vitro and in vivo, where repair of severed nerves and restoration of function may be more rapid using nerve guides or fiber nerve guides employing the inventive antibody. In vitro, NCAM16.2 provides a means for improving the rate and extent of neurite outgrowth, thereby shortening the time required to obtain results of experiments on nerve growth and its regulation. NCAM16.2 may also be labeled with a detectable label as is known in the art to provide a tracer antibody for detection of NCAM (and particularly the Ig-3 domain) in cells or in cell extracts. As blocking of an epitope in the Ig-3 domain of NCAM by binding to NCAM16.2 appears to further enhance the growth promoting activity of NCAM, study of the regulatory role of this epitope is of significant interest for therapeutic use of NCAM and NCAM16.2 in nerve regeneration. The availability of an antibody which recognizes this newly identified epitope of NCAM provides a tool for conducting such studies.

The following experimental examples are provided to illustrate certain specific embodiments of the invention and are not intended to limit the invention as defined by the appended claims.

In Examples 1–4 rat dorsal root ganglia were prepared as follows: Dorsal root ganglia (DRG) from embryonic, neonatal, or adult rats were dissected into sterile Hank's balanced salt solution (HBSS). The DRG were mildly digested with collagenase (1 mg/ml) and hyaluronidase (0.5 mg/ml) for 15–20 min. at 37° C. Embryonic and neonatal DRG were squeezed onto sutures. For adult DRG the coated suture was sewn through the ganglia. The DRG were grown in medium at 37° C. and observed at intervals. The proteins used as substrates for neurite outgrowth were obtained as follows: Human laminin and bovine serum albumin (BSA) were purchased from Sigma Chemical Company (St. Louis, Mo.). Mouse monoclonal antibody (MAb) NCAM16.2 was purified on Protein A-Sepharose. Human cell adhesion molecules (N-CAM, L1-Antigen and contactin) were purified from adult brain tissue by immunoaffinity chromatography on the appropriate immobilized MAb.

The proteins were covalently coupled to the nylon sutures as follows: Method 1 (acid hydrolysis)—Suture grade nylon, three-ply, size 10:0, was purchased from Ashaway Line and Twine (Ashaway, R.I.). It was hydrolyzed with HCl to generate free amino groups and reacted with glutaraldehyde to yield an activated nylon (see Hornby and Goldstein, 1976, Meth. Enzymol. 44:121). In an additional, optional step, the activated nylon was reacted with polyacrylamide hydrazide to yield nylon containing multiple reactive groups. Proteins to be coupled were oxidized with sodium periodate and dialyzed against 50 mM sodium acetate pH 4.5. The oxidized proteins were incubated with the activated nylon overnight at 4° C. Remaining active sites were blocked with 1% BSA in TBST for 3 hr. at room temperature. The derivatized and blocked fibers were then washed several times with sterile HBSS containing penicillin and streptamycin before use. Method 2 (O-alkylation) - Nylon as in Method 1 was O-alkylated and reacted with adipic dihydrazide to generate reactive hydrazide groups (1976, Meth. Enzymol. 44:122). Proteins were coupled and blocked as above. Method 3 (O-alkylation with polyacrylamide) - Nylon was O-alkylated as in Method 2 but the fibers were then reacted with polyacrylamide hydrazide instead of adipic dihydrazide to generate multiple hydrazide groups for reacting with oxidized protein.

In Examples 1–4 neurite outgrowth was estimated by observing the cultures under the microscope and estimating the percent of the total field covered.

EXAMPLE 1

To compare the growth promoting effects of NCAM16.2 to known positive regulators of neuronal outgrowth, day 2 postnatal (P2) rat DRG were mildly digested and squeezed onto sutures. The growth medium was changed on day six of culturing. Method 1 was used to couple the regulatory molecules and factors to the sutures. The results of the experiment are summarized in the following Table:

| PROTEIN COAT | NO. OF GANGLIA | RESULTS |
| --- | --- | --- |
| BSA | 1 | day 2 - little growth |
|  |  | day 5 - 0.5 mm |
|  |  | day 7 - 0.5 mm |
|  |  | day 14 - 1.5 mm |
| Contactin | 1 | day 2 - sig. outgrowth |
|  |  | day 5 - 0.5–2.0 mm |
|  |  | day 14 - 2.5 mm |
| Mab NCAM 16.2 | 3 | day 2 - some outgrowth |
|  |  | day 7 - 2.0–3.0 mm |
|  |  | day 14 - 3.5–5.0 mm |

As early as day 5, the sutures coated with a positive protein regulator of neurite outgrowth (contactin) and an antibody to a positive regulator of neurite outgrowth (Mab NCAM16.2) showed increased outgrowth as compared to sutures coated with BSA. Mab NCAM16.2 was unexpectedly found to the superior to contactin for increasing the rate of outgrowth.

EXAMPLE 2

Positive regulators or neurite outgrowth were compared using an alternative covalent coupling method. Postnatal day 0 rat DRG were squeezed onto nylon sutures prepared according to Method 2 (O-alkylation). The results were as shown in the following Table. Outgrowth measurements represent the average of multiple sutures prepared with each coating:

| PROTEIN COAT | DAY 4 OUTGROWTH (mm) | DAY 5 OUTGRWOTH (mm) |
| --- | --- | --- |
| Laminin | 0.8 | 1.4 |
| BSA | 0.6 | 0.8 |
| L1 Antigen | 0.9 | 1.4 |
| MAb NCAM 16.2 | 2.6 | 3.2 |
| Contactin | 0.9 | 1.4 |
| N-CAM | 2.0 | 2.2 |
| No protein | 0.7 | 0.8 |

All sutures coated with positive regulators showed increased rates of neurite outgrowth as compared to BSA coatings and uncoated sutures. The differences were most pronounced at Day 5. At Day 4 laminin, L1 antigen and contactin showed measurable but only minimal improvement. However, by Day 5 these same molecules promoted significantly increased neurite outgrowth. Again, however, the extent of outgrowth was significantly higher at both day 4 and day 5 on sutures coated with NCAM16.2 than on sutures coated with the conventional positive growth regulators. The results are depicted graphically in FIG. 1.

EXAMPLE 3

Figure 2:
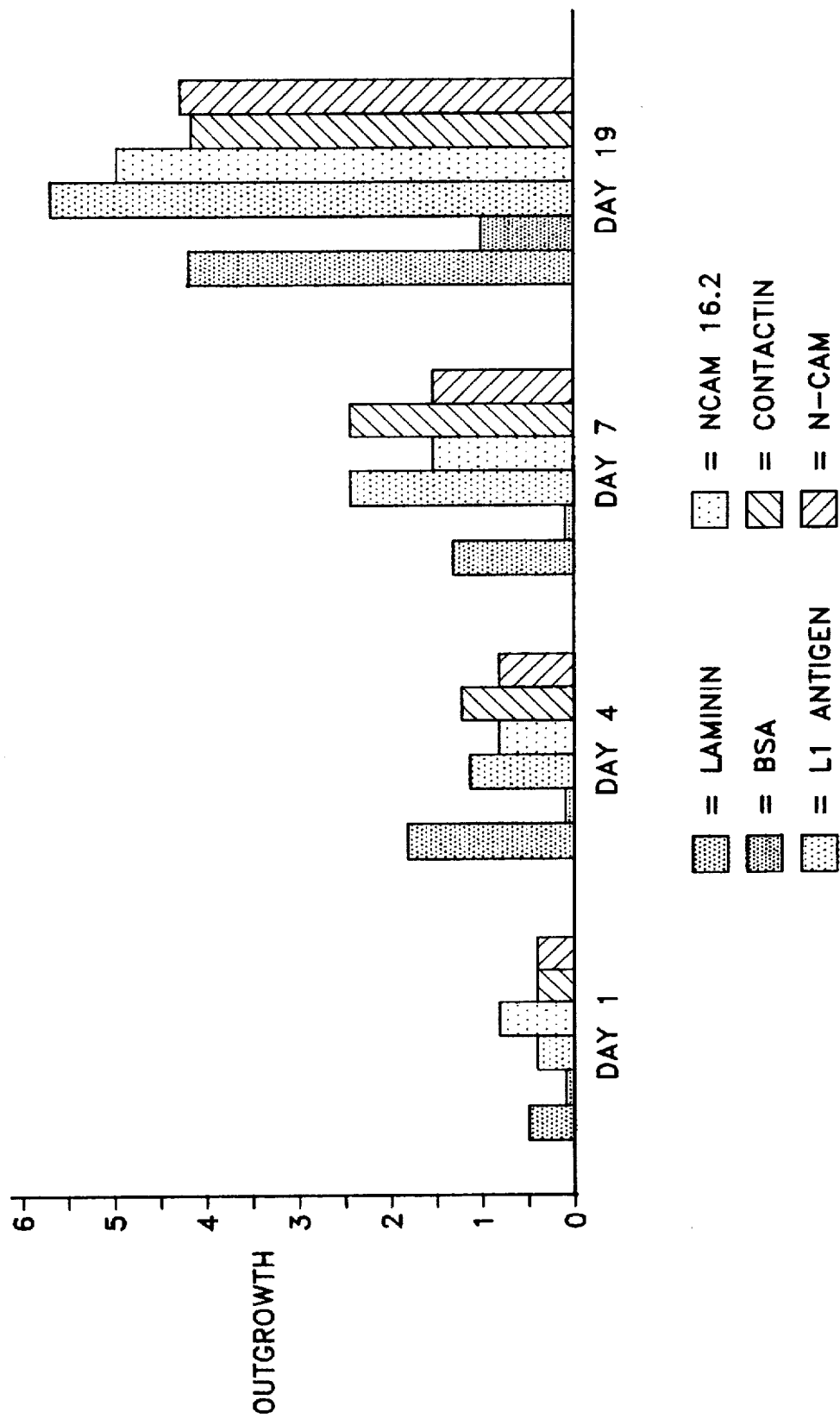
FIG. 2 is a graph of the data generated in Example 3 comparing the performance of fiber nerve guides having different neuronal regulatory molecules on the surface.

Late embryonic rat DRG were squeezed onto nylon sutures prepared according to Method 2 (O-alkylation). The results for neurite outgrowth rates are shown in the following Table and depicted graphically in FIG. 2.

| PROTEIN COAT | DAY 1 (mm) AVG.(S.D.) | DAY 4 (mm) AVG.(S.D.) | DAY 7 (mm) AVG.(S.D.) | DAY 19 (mm) AVG.(S.D.) |
| --- | --- | --- | --- | --- |
| Laminin | 0.5(0.1) | 1.8(1.5) | 1.3(1.2) | 4.1(1.2) |
| BSA | 0.1(0.1) | 0.1(0.1) | 0.1(0.1) | 1.0(1.7) |
| L1 Antigen | 0.4(0.2) | 1.1(0.8) | 2.4(1.3) | 5.6(1.9) |
| MAb NCAM 16.2 | 0.8(0.4) | 0.8(0.7) | 1.5(1.0) | 4.9(2.1) |
| Contactin | 0.4(0.2) | 1.2(0.9) | 2.4(0.4) | 4.1(1.3) |
| N-CAM | 0.4(0.2) | 0.8(0.2) | 1.5(0.6) | 4.2(1.4) |

As early as Day 1 of culture, neurite outgrowth on sutures coated with positive regulators was significantly improved as compared to outgrowth on BSA coated sutures. Again, the antibody directed against NCAM unexpectedly also provided increased rates of neurite outgrowth. The positive effect of NCAM16.2 was more comparable to that of conventional positive regulators in this study, and may reflect differences in biological activity on embryonic nerve cells as compared to postnatal nerve cells.

EXAMPLE 4

Figure 3:
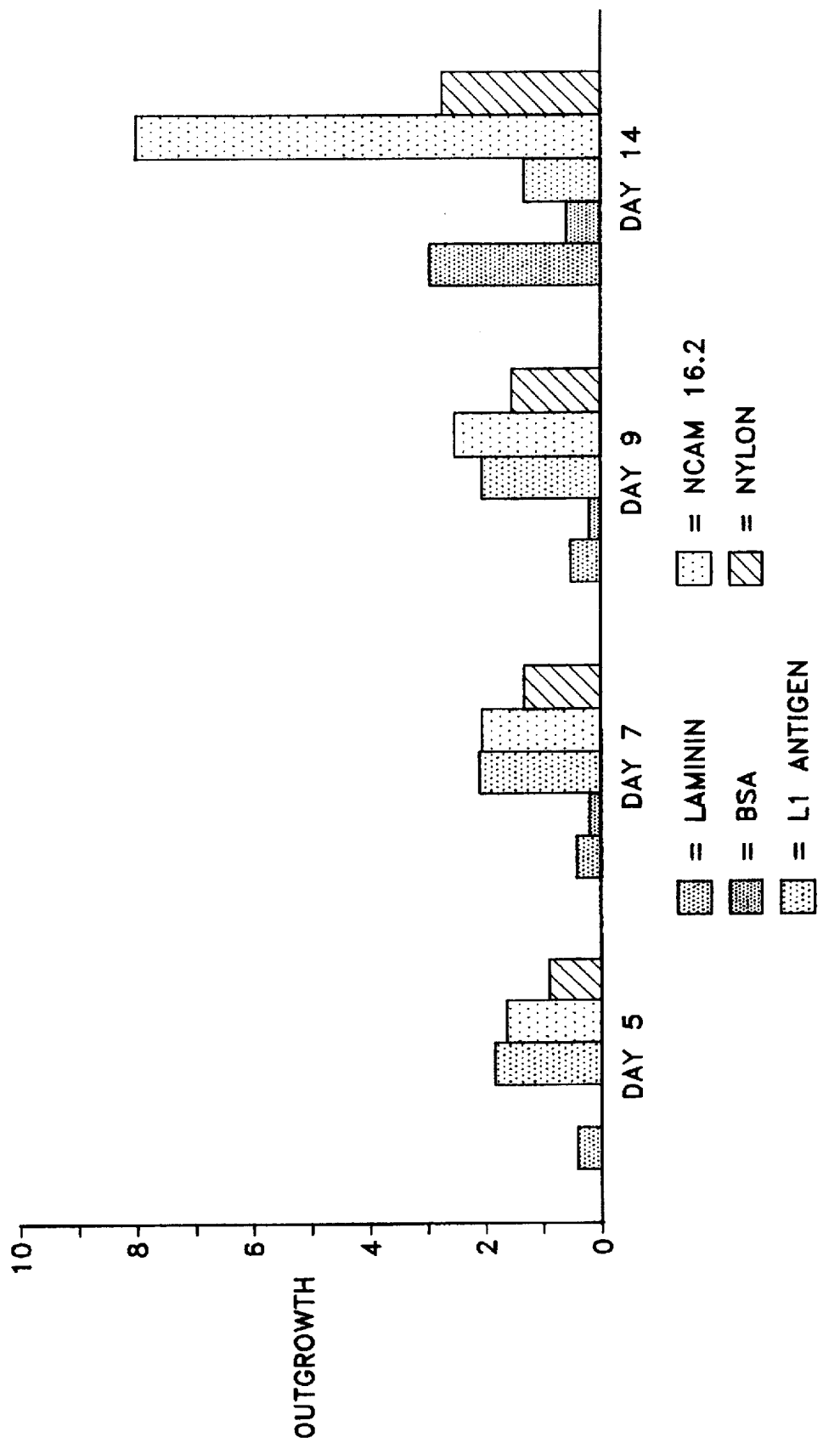
FIG. 3 is a graph of the data generated in Example 4 comparing the performance of fiber nerve guides having different neuronal regulatory molecules on the surface.

Adult rat DRG were prepared and the sutures sewn through. Regulatory proteins were coupled to the sutures using Method 2 (O-alkylation). Results were as shown in the following and are depicted graphically in FIG. 3:

| PROTEIN COUPLED | DAY 5 (mm) | DAY 7 (mm) | DAY 9 (mm) | DAY 14 (mm) |
| --- | --- | --- | --- | --- |
| Laminin | 0.4 | 0.4 | 0.5 | 2.9 |
| BSA | 0.0 | 0.2 | 0.2 | 0.6 |
| L1 Antigen | 1.8 | 2.1 | 2.5 | 6.2 |
| MAb NCAM 16.2 | 1.6 | 2.0 | 2.5 | 8.0 |
| None | 0.9 | 1.3 | 1.5 | 2.7 |

In this experiment laminin provided no outgrowth advantage over uncoated sutures. However, L1 Antigen and MAb NCAM16.2 significantly accelerated neurite outgrowth as compared to the controls. The NCAM16.2 effect on outgrowth was significantly more pronounced than that of L1 antigen by day 14. The sutures which had no coupled protein were prepared through the activation step of Method 2. Comparison of the activated sutures to the BSA coated sutures shows that activation itself improved the rate of neurite outgrowth, even in the absence of a nerve regulatory factor.

EXAMPLE 5

The rat sciatic nerve model was used to determine whether NCAM16.2 also has positive effects on the rate and extent of nerve regeneration in vivo. The protocol was generally as described by P. G. Cordeiro, et al. (1989, *Plastic and Reconstructive Surgery* 83:1013–1020). The sciatic nerve of adult male Fisher 344 rats was transected unilaterally at mid-thigh level and a 5 mm section of the nerve was removed. The nerve was repaired with a 10 mm polyethylene tube filled with one of two antibodies (an anti-Chlamydia control antibody and NCAM16.2, 10 animals each).

Animals were sacrificed two weeks after tube implantation and the tissue was processed as follows to display the number of myelinated axons at mid-tube level. Under deep Detamine anesthesia the animals were transcardially perfused with heparinized phosphate buffered saline (pH 7.2), followed by 1% glutaraldehyde and 2% paraformaldehyde in 0.1M phosphate buffer (pH 7.2). The sciatic nerve, including the entubulation repair, was exposed between the sciatic notch and the popliteal fossa and removed over a length of 1.5 cm distally from the sciatic notch. Post fixation was performed in 2% glutaraldehyde in 0.1M phosphate buffer (pH 7.2) for 24 hrs. at 4° C., followed by 2% osmium tetroxide in 0.1M phosphate buffer for 2 hrs. at room temperature. The tissues were embedded, with propylene oxide as the intermediate solvent, in Epon 812 resin. Sections were cut for light microscopy from the central region of the regenerated nerve cable that had formed within the entubulation repair. One micron transverse sections were cut and stained with toluidine blue and examined with a Zeiss Axiophot light microscope.

The number of myelinated axons was determined using a computer-based morphometric system. Images were digitized using a Macintosh based video digitizer and the Image 1.4 image analysis program (NIH). The cross-sectional area and thickness of the perineural layer was measured for each regenerated cable. Myelinated axons were counted within 62.3 µm by 47.5 µm sectors (total area=2960.5 µm$^2$) in a 47.5 µm wide centrally located band across each regenerated cable. Maturation and remyelination of the regenerated cable. Maturation and remyelination of the regenerated axons occur at the greatest rate within the core of the regenerated cable. The area of the regenerated cable containing remyelinated axons increases over time and is eventually limited by the peripheral boundary of the "perineural" layer. For accuracy, methods for estimating the population of myelinated axons within the cable should account for the myelinated axons occurring within a limited region of the total cable cross-sectional area. The method employed in this study used the number of sampling frames in which myelinated axons are detected to estimate the diameter (in number of frames) of the central area containing myelinated axons. The myelinated axon density was calculated by dividing the total number of axons observed by the number of frames in which axons were detected, resulting in the number of myelinated axons/sample frame (axons/2960.5 µm$^2$). From the myelinated axon density and the area of the central myelinated axon containing region, the total number of myelinated axons was estimated. Differences among groups were analyzed using an unpaired t-test as well as a Wilcoxon signed-rank test.

Figure 4:
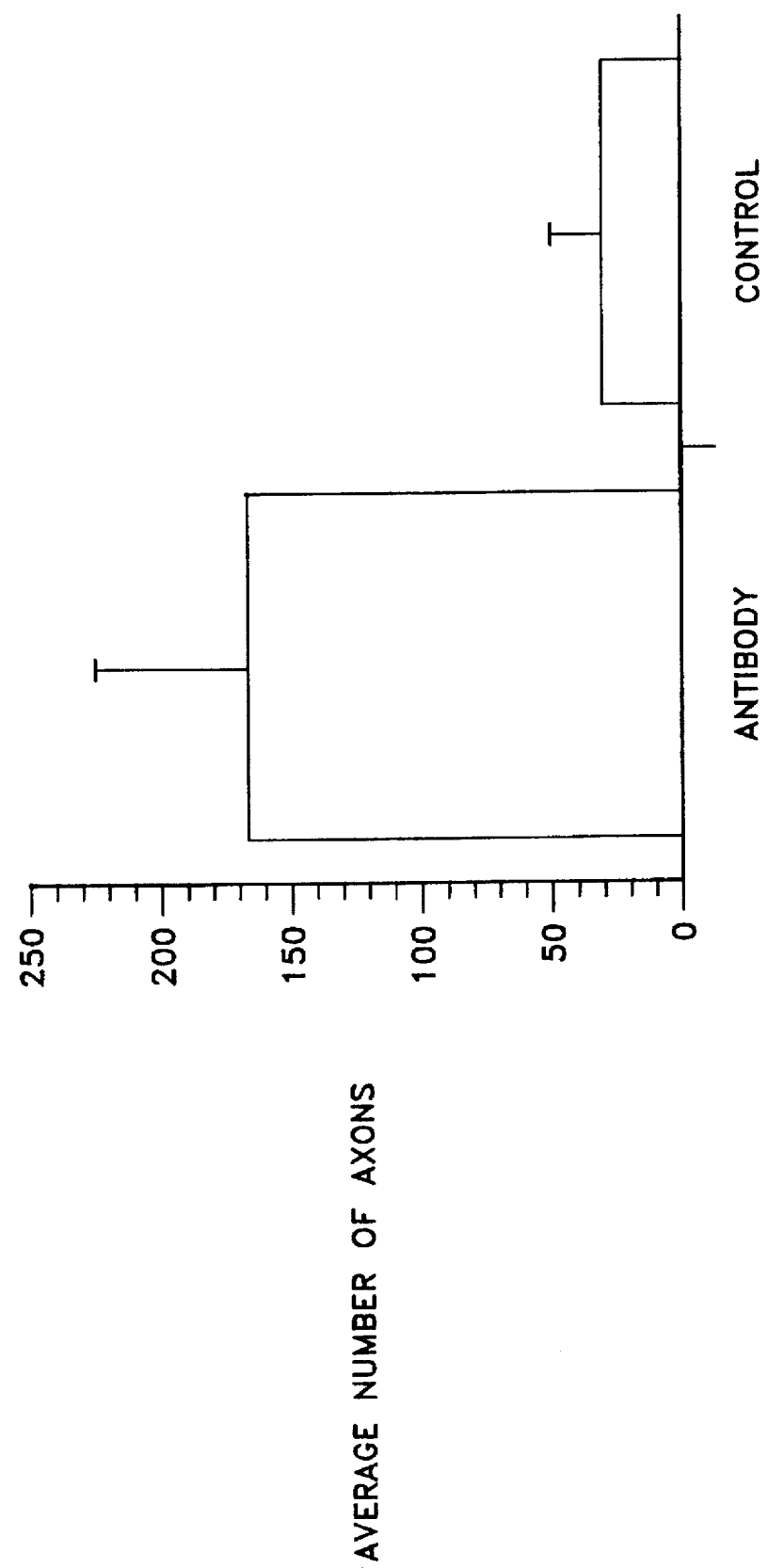
FIG. 4 is a graph of the data generated in Example 5 comparing the performance of NCAM16.2 to a control antibody in vivo.

The results are shown in FIG. 4. There were significantly more axons in the group of animals which received NCAM16.2 than in the control (p<0.5). Approximately 55% of the control animals did not display any myelinated axons at the two week time point vs. only 30% of the animals receiving NCAM16.2. This study was designed to evaluate the very early stages of regeneration, and the results show a clear stimulatory effect of NCAM16.2 on initial axonal outgrowth. The in vivo study complements the in vitro studies and shows that in this model system NCAM16.2 significantly enhances early axonal regeneration across a 5 mm nerve gap distance. These results also suggest that NCAM16.2 may enhance bridging of even longer nerve gap distances, making this antibody useful for improving nerve regeneration in primates where nerve gap distances of 5–10 cm are not uncommon.

What is claimed is:

1. A method for detecting N-CAM comprising contacting a cell or a cell extract containing N-CAM with monoclonal antibody NCAM16.2 and detecting the presence of the N-CAM by detecting binding of the monoclonal antibody NCAM16.2 to the N-CAM.

2. The method of claim 1 wherein binding of monoclonal antibody NCAM16.2 to the N-CAM is detected by means of a detectable label.

3. The method of claim 2 wherein monoclonal antibody NCAM16.2 is labeled with the detectable label.

* * * * *